US010905602B2

(12) United States Patent
Olsson et al.

(10) Patent No.: US 10,905,602 B2
(45) Date of Patent: Feb. 2, 2021

(54) ARRAY OF GENDER-SPECIFIC ABSORBENT ARTICLES

(71) Applicant: Essity Hygiene and Health Aktiebolag, Gothenburg (SE)

(72) Inventors: Anna Klinte Olsson, Gothenburg (SE); Lucas Bäck, Gothenburg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 16/462,772

(22) PCT Filed: Nov. 23, 2016

(86) PCT No.: PCT/SE2016/051157
§ 371 (c)(1),
(2) Date: May 21, 2019

(87) PCT Pub. No.: WO2018/097772
PCT Pub. Date: May 31, 2018

(65) Prior Publication Data
US 2019/0314215 A1    Oct. 17, 2019

(51) Int. Cl.
*A61F 13/49* (2006.01)
*A61F 13/496* (2006.01)
(Continued)

(52) U.S. Cl.
CPC ...... *A61F 13/491* (2013.01); *A61F 13/15593* (2013.01); *A61F 13/49001* (2013.01);
(Continued)

(58) Field of Classification Search
CPC .............. A61F 13/491; A61F 13/49019; A61F 2013/49026; A61F 2013/49028;
(Continued)

(56) References Cited

U.S. PATENT DOCUMENTS 4,326,302 A    4/1982  Lowe et al.
5,735,839 A *  4/1998  Kawaguchi ....... A61F 13/49009
                                              604/385.29
(Continued)

FOREIGN PATENT DOCUMENTS

CN    1177471 A    4/1998
CN    101677879 A  3/2010
(Continued)

OTHER PUBLICATIONS

International Search Report and Written Opinion for International Application No. PCT/SE2016/051157, dated Jun. 22, 2017—13 pages.
(Continued)

*Primary Examiner* — Ophelia A Hawthorne
*Assistant Examiner* — Heather K Barnwell
(74) *Attorney, Agent, or Firm* — Buchanan Ingersoll & Rooney P.C.

(57) ABSTRACT

An array of gender-specific disposable absorbent articles is provided. The array has a first disposable absorbent article adapted to be worn by males and a second disposable article adapted to be worn by females. Both articles have in their longitudinal direction, a front portion, a back portion and a crotch portion between the front portion and the back portion. The first article has a first elastic component configured for providing fit and comfort to a male user. The second article has a second elastic component configured for providing fit and comfort to a female user. The first and the second elastic components each have a plurality of elastic elements extending at least partly along each respective article. The first and second elastic components differ from each other in at least the positioning or the elastic strength of the respective elastic elements. A method for manufacturing the array is also provided.

16 Claims, 5 Drawing Sheets

(51) Int. Cl.
*A61F 13/511* (2006.01)
*A61F 13/514* (2006.01)
*A61F 13/491* (2006.01)
*A61F 13/15* (2006.01)
*A61F 13/53* (2006.01)

(52) U.S. Cl.
CPC ...... *A61F 13/496* (2013.01); *A61F 13/49011* (2013.01); *A61F 13/49012* (2013.01); *A61F 13/4915* (2013.01); *A61F 13/511* (2013.01); *A61F 13/514* (2013.01); *A61F 13/53* (2013.01); *A61F 2013/49025* (2013.01); *A61F 2013/49026* (2013.01); *A61F 2013/49028* (2013.01); *A61F 2013/49074* (2013.01); *A61F 2013/49084* (2013.01)

(58) Field of Classification Search
CPC ............ A61F 13/4915; A61F 13/15593; A61F 13/49012; A61F 13/49001; A61F 13/49011; A61F 13/496; A61F 13/511; A61F 13/514; A61F 13/53; A61F 2013/49025
See application file for complete search history.

(56) References Cited

U.S. PATENT DOCUMENTS

| | | | |
|---|---|---|---|
| 6,056,732 A | 5/2000 | Fujioka et al. | |
| 6,083,212 A * | 7/2000 | Kumasaka | A61F 13/496 604/358 |
| 2007/0142806 A1 * | 6/2007 | Roe | A61F 13/49015 604/385.01 |
| 2007/0233027 A1 | 10/2007 | Roe et al. | |
| 2008/0275415 A1 | 11/2008 | Wheeler et al. | |
| 2009/0264851 A1 | 10/2009 | Richlen et al. | |
| 2010/0108554 A1 * | 5/2010 | Melius | A61F 13/491 206/438 |
| 2011/0125122 A1 | 5/2011 | Thorson et al. | |
| 2012/0323204 A1 | 12/2012 | Poole et al. | |
| 2013/0060219 A1 | 3/2013 | Mukai et al. | |
| 2013/0079743 A1 | 3/2013 | Mukai et al. | |
| 2014/0018757 A1 | 1/2014 | De Bruin et al. | |
| 2015/0320614 A1 | 11/2015 | Seitz et al. | |
| 2015/0366724 A1 | 12/2015 | Fukuzawa et al. | |
| 2016/0128875 A1 * | 5/2016 | Ichikawa | A61F 13/4915 604/385.16 |
| 2016/0166444 A1 * | 6/2016 | Finlayson | A61F 13/49017 604/385.11 |
| 2016/0220425 A1 | 8/2016 | Zink et al. | |

FOREIGN PATENT DOCUMENTS

| | | |
|---|---|---|
| CN | 102202628 A | 9/2011 |
| CN | 105007878 A | 10/2015 |
| EP | 0824906 B1 | 2/1998 |
| EP | 0865780 A2 | 9/1998 |
| EP | 1537842 A1 | 6/2005 |
| GB | 2259441 A | 3/1993 |
| JP | H04242643 A | 8/1992 |
| JP | H0564651 A | 3/1993 |
| JP | 2002159529 A1 | 6/2002 |
| JP | 2005279077 A | 10/2005 |
| JP | 2011517985 A | 6/2011 |
| JP | 2012130585 A | 7/2012 |
| JP | 2014150909 A | 8/2014 |
| WO | 2008135870 A1 | 11/2008 |
| WO | 2009128029 A2 | 10/2009 |
| WO | 2010052597 A2 | 5/2010 |
| WO | 2013153756 A1 | 10/2013 |
| WO | 2016029566 A1 | 3/2016 |
| WO | 2016032456 A1 | 3/2016 |

OTHER PUBLICATIONS

International Preliminary Report on Patentability for International Application No. PCT/SE2016/051157, dated Nov. 7, 2018—5 pages.
Chinese Office Action for Chinese Application No. 201680090985.9, dated Oct. 21, 2019, with translation, 15 pages.
Office Action (Notification of the Second Office Action) dated May 12, 2020, by the China National Intellectual Property Administration (CNIPA) of the People's Republic of China in corresponding Chinese Patent Application No. 201680090985.9, and an English Translation of the Office Action. (11 pages).
Search Report and Written Opinion dated May 18, 2020, by the Brazilian Patent Office in Brazilian Patent Application No. BR112019008214-0. (4 pages).
Office Action (Notice of Reasons for Rejection) dated Jul. 13, 2020 by the Japanese Patent Office in Corresponding Japanese Patent Application No. 2019-527510, and an English Translation of the Office Action. (5 pages).

\* cited by examiner

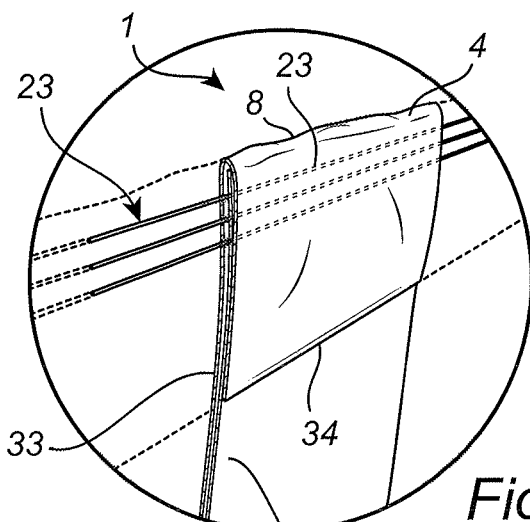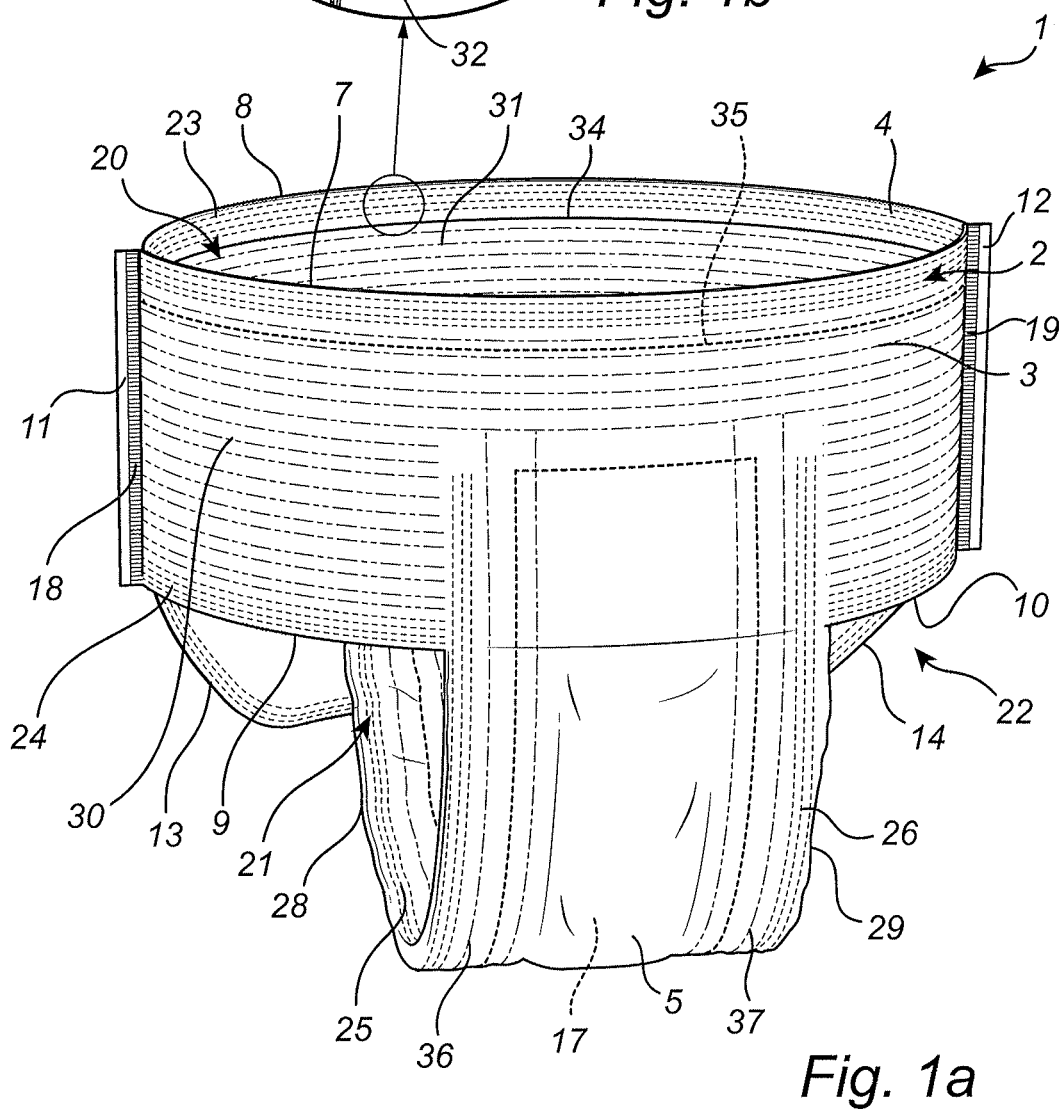
Fig. 1b
Fig. 1a

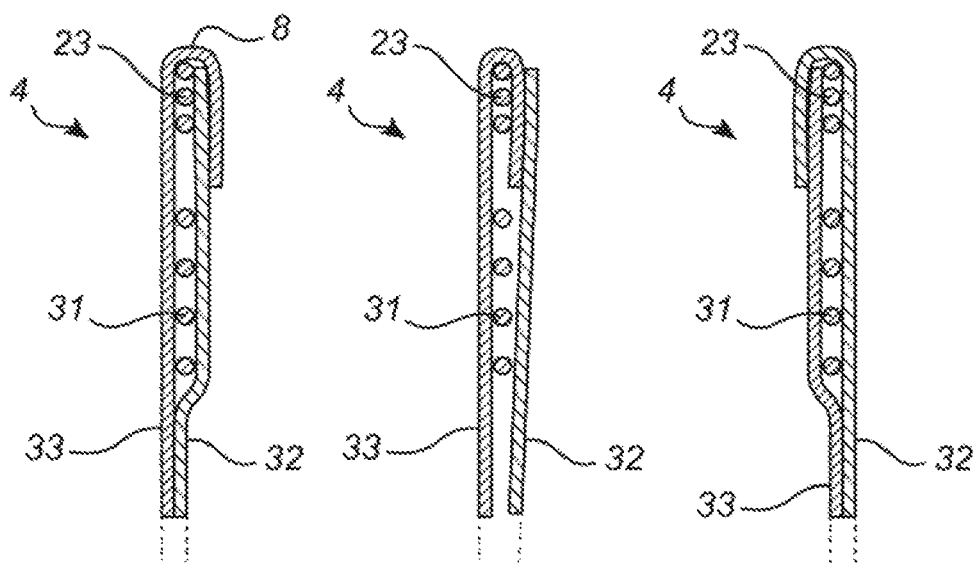
*Fig. 4a*   *Fig. 4b*   *Fig. 4c*
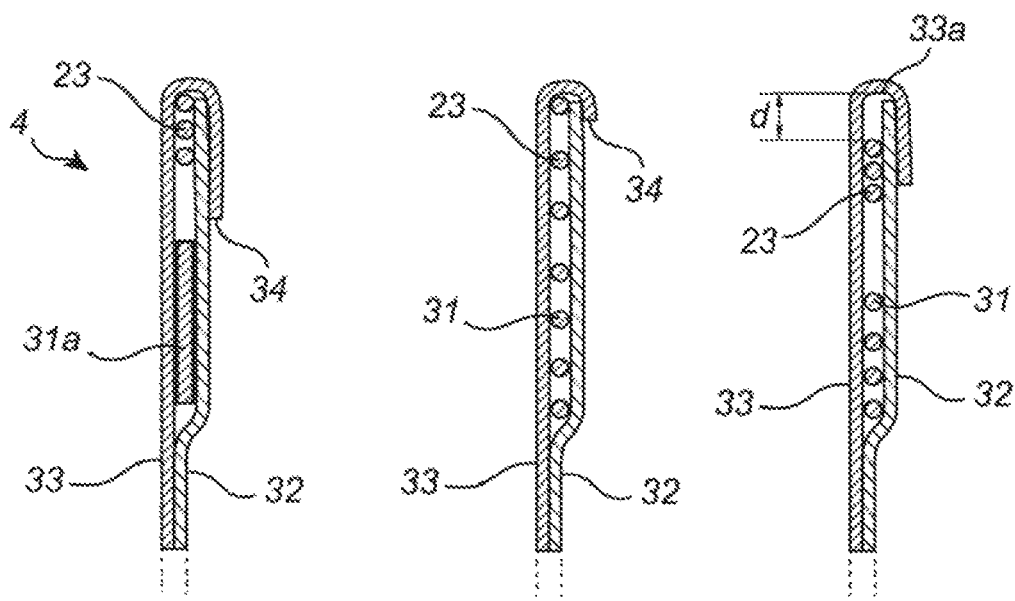
*Fig. 4d*   *Fig. 4e*   *Fig. 4f*
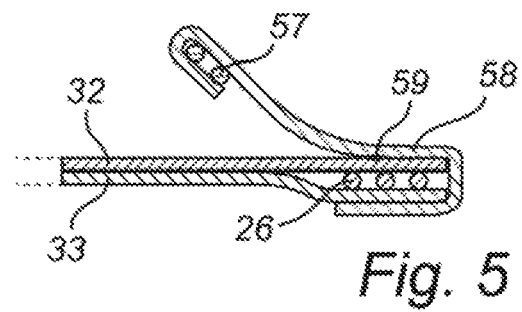
*Fig. 5*

ARRAY OF GENDER-SPECIFIC ABSORBENT ARTICLES

CROSS REFERENCE TO RELATED APPLICATIONS

This is a U.S. National Phase application of PCT/SE2016/051157, filed Nov. 23, 2016, the disclosure of which is incorporated herein by reference in its entirety for all purposes.

TECHNICAL FIELD

The invention relates to an array of gender-specific disposable absorbent articles, said array comprising: a first disposable absorbent, article adapted to be worn by males, the article having, in its longitudinal direction, a front portion, a back portion and a crotch portion between the front portion and the back portion, and a first elastic component configured for providing fit and comfort of the article to a male user; and a second disposable absorbent article adapted to be worn by females, the article having, in its longitudinal direction, a front portion, a back portion and a crotch portion between the front portion and the back portion, and a second elastic component configured for providing fit and comfort of the article to a female user. Furthermore, the first elastic component and the second elastic component comprise a plurality of elastic elements extending at least partly along each article.

The invention also relates to a method for manufacturing an array of gender-specific disposable absorbent articles, said method comprising: providing a first disposable absorbent article adapted to be worn by males, the article having, in its longitudinal direction, a front portion, a back portion and a crotch portion between the front portion and the back portion, and a first elastic component configured for providing fit and comfort of the article to a male user; and providing a second disposable absorbent article adapted to be worn by females, the article having, in its longitudinal direction, a front portion, a back portion and a crotch portion between the front portion and the back portion, and a second elastic component configured for providing fit and comfort of the article to a female user; and also providing a plurality of elastic elements forming part of said first elastic component and said second elastic component and extending at least partly along each article.

BACKGROUND

Disposable absorbent articles, for example in the form of incontinence liners, baby diapers and sanitary napkins, are well known. The general purpose of such absorbent articles is to absorb, distribute and store various types of body exudates, while providing a high level of comfort and sense of dryness to the wearer during use of the absorbent article. Also, such an absorbent article is configured to prevent the wearer from getting the clothes soiled by such body exudates.

Absorbent articles in the form of incontinence articles are used to protect a wearer against urine leakage. An incontinence article can be configured for example as a pant diaper, a sanitary pant or an incontinence pant adapted for use by a baby, child or adult, male or female user. Also, an incontinence article is designed with an absorption capacity which is adapted to absorb the fluid that is expected to be released into the article when it is worn. Incontinence articles are used to assist persons with incontinence so that they can maintain a normal lifestyle without any inconvenience caused by incontinence.

With regard to adult users of pant-type incontinence articles, there is a particular demand for such articles which are adapted to the male and female anatomy, respectively. For example, it is known that men and women have different anatomy and different skeletal configuration. Also, for male persons using incontinence articles, it can be expected that urine is discharged at the front portion of the article, whereas for female persons, it can be expected that urine is discharged at a lower portion of the article. For this and other reasons, there is a need to adapt such incontinence articles to male and female users.

Furthermore, there is a demand for incontinence articles which are designed in a manner so that they resemble regular underwear. In fact, adult persons who use incontinence articles may be reluctant to use articles which are "diaper-like" and which are perceived as bulky, uncomfortable and unattractive, and which may be visible if, for example, the user wears tight clothes over an incontinence article. This means that there is a desire to provide incontinence articles which are less bulky and which have a look and feel which is similar to traditional underwear.

Also, there is a desire to provide incontinence articles which are stylish and attractive for both men and women and which follow the anatomy and body contour of a male and female body. In this manner, a more discreet article can be provided which gives the wearer a higher level of self-confidence, comfort and self-esteem and which provides incontinence protection for users having different lifestyles.

In summary, there is a need for an assortment, or array, of incontinence articles which can be adapted to male and female users, respectively, in an optimal manner as regards the fit, comfort and function. Furthermore, there is a need for efficient manufacturing methods for producing such an array of articles, in particular in a way so that no time-consuming and costly adjustments or modifications of the manufacturing process need to be done for example during a change from production of a male article to a female article, and vice versa.

The patent document US 2009/264851 discloses an array of disposable absorbent articles having containment flaps which are adapted to the male and female anatomy, respectively. More precisely, the containment flaps of the male-type articles differ from the containment flaps of the female-type articles in at least one structural feature, such as for example the flap active length, flap tension and flap height.

Although the array of articles disclosed in US 2009/264851 is generally intended to solve the above-mentioned problem of adapting absorbent articles to male and female users, there exists a need for further improvements of absorbent articles, in particular incontinence articles, so as to provide such articles which are adapted to male and female users while still allowing an efficient manufacturing process wherein changes in the production between a male to a female model can be carried without any significant interruptions or time-consuming modifications.

SUMMARY

An object with the present invention is to provide an array of gender-specific absorbent articles, and a method for manufacturing thereof, which is adapted to male and female users and which follow requirements as to comfort, fit and design of male and female users and which also can be manufactured by means of an efficient manufacturing process.

In accordance with the invention, the above-mentioned object is obtained by means of an array of gender-specific disposable absorbent articles, said array comprising: a first disposable absorbent article adapted to be worn by males, the article having, in its longitudinal direction, a front portion, a back portion and a crotch portion between the front portion and the back portion, and a first elastic component configured for providing fit and comfort of the article to a male user; and a second disposable absorbent article adapted to be worn by females, the article having, in its longitudinal direction, a front portion, a back portion and a crotch portion between the front portion and the back portion, and a second elastic component configured for providing fit and comfort of the article to a female user; said first elastic component and said second elastic component comprising a plurality of elastic elements extending at least partly along each article. Furthermore, the first elastic component and the second elastic component differ from each other in at least the positioning or the elastic strength of said elastic elements.

The array according to the invention provides certain advantages due to the fact that it comprises articles which are adapted to the male and female anatomy and which can also be manufactured with an efficient manufacturing process.

According to an embodiment, the array is arranged so that the first elastic element and the second elastic element are arranged as a plurality of elastic threads extending in a generally parallel manner along said article and differing from each other in the distance between adjacent elastic threads. This means that a manufacturing process can be implemented in a manner so that a change between production of a male and a female product can be carried out in a simple manner by changing the distance between the elastic threads.

According to an embodiment, the first elastic element and second elastic element are configured with different dimensions, material or elastic force, so as to provide said different elastic strength. This means that a manufacturing process can be implemented in a manner so that a change between production of a male and a female product can be carried out in a simple manner by changing the type of elastic threads which form the elastic elements of the articles.

According to an embodiment, the elastic components form part of at least the back portion of the first absorbent article and the back portion of the second absorbent article, respectively. Furthermore, according to an embodiment, the elastic threads are divided into an upper section and a lower section and wherein the above-mentioned differences in at least the positioning or the elastic strength of said elastic elements are provided in the lower section.

Furthermore, the above-mentioned object of the invention is obtained by means of a method for manufacturing an array of gender-specific disposable absorbent articles, said method comprising: providing a first disposable absorbent article adapted to be worn by males, the article having, in its longitudinal direction, a front portion, a back portion and a crotch portion between the front portion and the back portion, and a first elastic component configured for providing fit and comfort of the article to a male user; and providing a second disposable absorbent article adapted to be worn by females, the article having, in its longitudinal direction, a front portion, a back portion and a crotch portion between the front portion and the back portion, and a second elastic component configured for providing fit and comfort of the article to a female user; and providing a plurality of elastic elements forming part of said first elastic component and said second elastic component and extending at least partly along each article. Furthermore, the method comprises: Providing a first elastic component and a second elastic component which are different from each other in at least the positioning or the elastic strength of said elastic elements.

BRIEF DESCRIPTION OF THE DRAWINGS

The invention will be described in greater detail below with reference to the figures shown in the appended drawings.

FIG. 1a shows a perspective front view of the absorbent article according to the disclosure;

FIG. 1b is a perspective view of an enlarged section of a waist edge forming part of the absorbent article;

FIGS. 4a-4f show cross-sectional views of alternative embodiments of the absorbent article according to the disclosure;

FIG. 5 shows a cross-sectional view of a crotch section of said absorbent article;

DETAILED DESCRIPTION OF PARTICULAR EMBODIMENTS

Different aspects of the present disclosure will be described more fully hereinafter with reference to the enclosed drawings. The embodiments disclosed herein can, however, be realized in many different forms and should not be construed as being limited to the aspects set forth herein.

Figure 2:
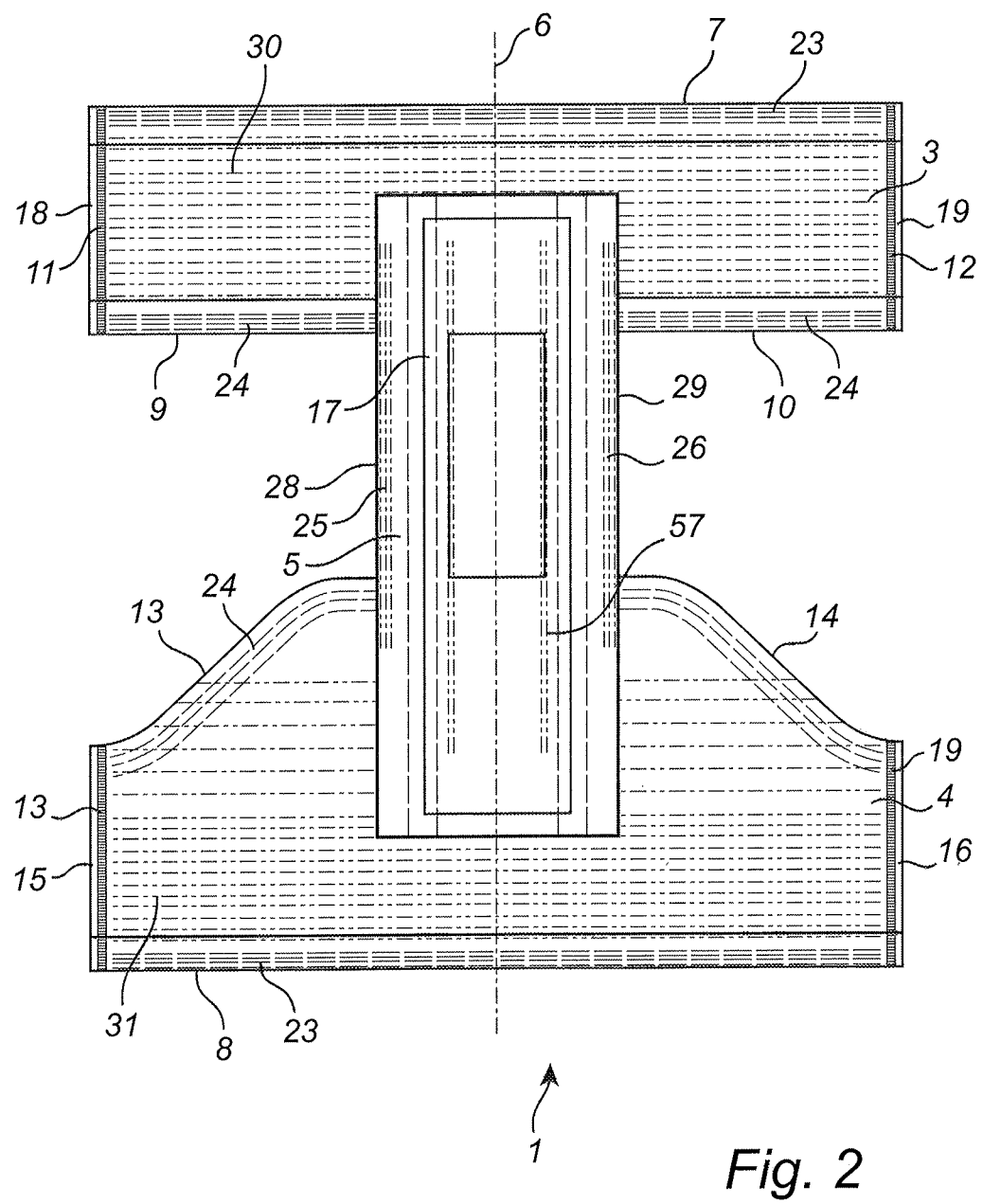
FIG. 2 shows a top view of the absorbent article.

With reference to FIG. 1a of the drawings, there is shown an embodiment of a disposable pant-type absorbent article 1 illustrated in an assembled and ready-to-use state. The same absorbent article 1 is also shown in FIG. 2, but in a condition in which it is laid out flat and as viewed from above in order to show its main components. Furthermore, FIG. 1b is a perspective view of an enlarged section of a part of the absorbent article 1, as will be described in greater detail below.

The disclosure relates to an array of gender-specific, disposable absorbent articles and the article 1 shown in FIGS. 1a, 1b and 2 is not intended to describe a specific male or female model, but is used to describe the general principles of an article which can be either suited for male or female users. However, FIGS. 6a and 6b, which will be described in detail below, disclose an array of articles and indicate the difference between male and female articles.

With reference to FIG. 1a and FIG. 2, the pant-type absorbent article 1 is for example in the form of a pant diaper, a sanitary pant or an incontinence pant adapted for use by a baby, child or adult, male or female user. The pant-type absorbent article 1 according to FIG. 1 comprises a single-piece chassis 2 having a front portion 3, a back portion 4, a crotch portion 5 connecting the front and back portions 3, 4, and a centre line 6 (see FIG. 2) in the longitudinal direction of the article. The absorbent article 1 has a longitudinal direction, a transverse direction and a thickness direction.

The front portion 3 has a waist edge 7, a pair of leg edges 9, 10 and a pair of side edges 11, 12. Furthermore, the back portion 4 has a waist edge 8, a pair of leg edges 13, 14 and a pair of side edges 15, 16.

As mentioned above, the absorbent article 1 comprises a crotch portion 5, which comprises an absorbent body 17 located mainly in said crotch portion 5. The absorbent body 17 may be manufactured separately from the chassis 2 and inserted and fastened to the chassis 2 at a suitable manufacturing step. This process will be described in greater detail below.

The side edges 11, 12 of the front portion 3 are attached to the opposite side edges 15, 16 of the back portion 4 by means of permanent or re-closable side connections 18, 19 such as side seams, hook and loop fasteners, adhesive fasteners, or the like, in order to at least partly define a waist opening 20 and a pair of leg openings 21, 22.

A first elastic element in the form of an elastic waist component 23 is fastened to the chassis 2 at least partly along the waist edges 7, 8 forming part of the front portion 3 and the back portion 4. The purpose of the elastic waist component 23 is to provide the absorbent article 1 with a good fit around the waist of the user wearing the article. The elastic waist component 23 is fastened relatively close to the waist edges 7, 8, around the waist opening 20.

Furthermore, a second elastic element in the form of an elastic leg component 24 is fastened to the chassis 2 at least partly along the leg edges 9, 10 of the front portion 2 for the purpose of providing the absorbent article 1 with a good fitting around the legs of the user wearing the article. The elastic leg component 24 is fastened relatively close to the leg edges 9, 10.

As shown in particular in FIG. 2, the elastic leg component 24 forms a straight line in the front portion 3 and has a curved configuration in the back portion 4.

Furthermore, a first absorbent body elastic 25 and a second absorbent body elastic 26 are arranged along the crotch portion 5. The first absorbent body elastic 25 is arranged along a first crotch edge 28 whereas the second absorbent body elastic 26 is arranged along a second crotch edge 29. In particular, the first absorbent body elastic 25 and the second absorbent body elastic 26 are arranged relatively close to the longitudinal crotch edges 28, 29. In a similar manner, the elastic waist component 23 and the elastic leg component 24 are also arranged relatively close to the waist edges 7, 8 and the leg edges 9, 10, respectively, as shown in FIG. 1 and FIG. 2.

If the elastic leg component 24 and the elastic waist component 23 are fastened at a location close to the leg and waist edges 7, 8, 9, 10, respectively, less non-elasticised web material is available at the leg and waist edges such that less frills is created along said edges. This is an advantage, since a large amount of material at the leg edges may be perceived as uncomfortable by a user and may give the user an impression that the article is not similar to conventional underwear.

Having the elastic leg feature 24 positioned closer to the leg edge 9, 10 may also result in an absorbent article 1 having an improved fit which corresponds to the shape of the legs of the user. It is thus desirable to provide an elasticised leg edge 9, 10 of the front and back portion 3, 4 that has a more cuff like appearance with less frills, thereby providing the absorbent article 1 with an appearance more similar to cloth underwear.

Furthermore, as shown in FIG. 1a and FIG. 2, the absorbent article 1 comprises a front elastic component 30 and a back elastic component 31 which are both based on a number of elastic threads mounted at a certain distance from each other in a generally parallel manner around the article 1, i.e. the region of the belly and the backside of the user. The purpose of these elastic components 30, 31 is to contribute to a good fit and comfort for the wearer of the article 1. In particular, the configuration of the elastic threads can be adapted to the male and female anatomy and the need for a suitable fit and comfort for male and female users of the article 1.

This disclosure is based on the principle that the positioning of the elastic threads and also the elastic properties of the elastic threads can be individually adapted so as to provide a configuration of the back elastic component 31 and front elastic component 30 which is arranged so as to individually fit the male and female anatomy, respectively. This will be described in greater detail below with reference to FIG. 6a and FIG. 6b. More precisely, the positioning of the elastic threads refers to the manner in which the threads are laid out, in a geometric sense, along the absorbent articles in the array and also the distance between any two adjacent elastic threads. According to a further embodiment, the number of elastic threads used can also be chosen so as to provide a configuration of the back elastic component 31 and front elastic component 30 which is arranged so as to individually fit the male and female anatomy, respectively.

Furthermore, and as mentioned above, it can be noted that a process of fastening the elastic waist component 23 and the elastic leg component 24 close to an edge of a web material, i.e. in this case close to the waist edges 7, 8 and the leg edges 9, 10, respectively, is difficult due to the manufacturing tolerances of the production line. The provision of elastic elements along the edges of the article, i.e. along the waist, legs and crotch edges, contributes to a modern and well-fitting absorbent article such as an incontinence article. Such elastic elements are normally provided with a number of elastic threads which are arranged along a waist edge, a leg edge and two crotch edges.

A production process for a pant-type absorbent article operates at a high rate and such a fully automatized manufacturing line needs to have certain tolerances. If the elastic threads of the elastic components are positioned too close to the corresponding edges, there is a risk that the threads may actually be laid and positioned outside the edges. Since glue is normally applied to the threads, there is a risk for production interruption if the elastic threads are erroneously positioned outside the actual edges of the article.

With further reference to FIG. 2 and also FIG. 1b, there is provided an embodiment in which the elastic waist component 23, the elastic leg component 24 and the elastic absorbent body components 25, 26 are fastened by means of a folding arrangement of the article 1 in question. The principles for this folding arrangement are shown in FIG. 1b, which shows an enlargement of a small section of the upper part of the back portion 4, more precisely a section of the absorbent article 1 close to the waist edge 8 of the back portion 4.

In a manner which is conventional as such, the absorbent article 1 comprises a liquid permeable topsheet 32, i.e. a sheet which is intended to face the user of the article 1, and a liquid impermeable backsheet 33, i.e. a sheet which is placed so as to face the garment worn by the user. Generally, the liquid permeable topsheet 32 comprises or consist of a nonwoven material. The topsheet material may further be composed of tow fibres, porous foams, apertured plastic films and similar materials. The materials suited as topsheet materials should be soft and non-irritating to the skin and should be readily penetrated by body fluid, e.g. urine or menstrual fluid, and display low rewetting properties.

Furthermore, the liquid impermeable backsheet 33 may consist of a thin plastic film, e.g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent article, while still preventing liquids from passing through the backsheet 33 material.

According to various embodiments, the materials which can be used for manufacturing the backsheet 33 include thin and flexible fluid impermeable plastic films, or fluid impermeable nonwoven materials, fluid impermeable foams and fluid impermeable laminates.

Furthermore, the backsheet 33 is formed by a single layer, and can alternatively be formed by a multi-layered structure, i.e. a laminate, wherein at least one layer is fluid impermeable. Furthermore, the backsheet 33 can optionally be elastic in either direction. According to further embodiments, the backsheet 33 may be breathable, implying that air and vapor may pass through the backsheet. Furthermore, the backsheet 33 may optionally have an outer, garment-facing surface of a textile material such as nonwoven.

The absorbent core 17 can be formed by a single layer consisting of fibres of cellulosic fluff pulp. According to alternative embodiments, the absorbent core 17 can be made up of any suitable absorbent or fluid-absorbing material as known in the art, for example foam, fiber waddings and similar materials.

Furthermore, the absorbent core 17 may consist of a mixture of cellulosic fluff pulp and a suitable amount of superabsorbent particles. Such superabsorbent material is well known in the field of absorbent articles, and is constituted by a water-swellable and water-insoluble material which is capable of absorbing large quantities of fluid upon formation of a hydrogel. Normal superabsorbent materials are capable of absorbing fluids of at least 10 times its own weight.

According to further embodiments, the absorbent core 17 may further incorporate components for improving the properties of the absorbent core. Some examples of such components are binder fibers, fluid-dispersing materials, fluid acquisition materials, etc. as known in the art. The absorbent core 17 may also be a homogeneous structure or may be a layered structure with laminates of the same or different materials. The absorbent layers may have uniform thickness or may vary in thickness in different parts of the layers.

The topsheet 32 and backsheet 33 may be connected to each other for example by adhesive bonding, gluing or welding by heat or ultrasonic. The topsheet 32 and/or the backsheet 33 may further be attached to the absorbent body by any method known in the art, such as adhesive, heat-bonding etc.

According to an embodiment, the topsheet and backsheet in the portions forming the front portion 3 and the back portion 4 may be of different type than the topsheet and backsheet in the crotch portion 5. In the latter case, it is suitable with a fluid-permeable topsheet and a fluid-impermeable backsheet (as described above) since in an embodiment, the absorbent article 1 must have absorbent properties in the crotch portion 5. However, in the parts forming the front portion 3 and the back portion 4, both the topsheet and the backsheet may be for example liquid-impermeable, since these parts of the absorbent article 1 generally do not need to have absorbent properties.

According to the embodiment shown in FIG. 1b, the backsheet 33 is configured so that it can be folded along the waist edge 8 of the back portion 4 and over the topsheet 32. In this manner, the elastic waist component 23 is at least partly enclosed between the topsheet 32 and the backsheet 33. More precisely, the elastic waist component 23 is positioned between the backsheet 33 and the topsheet 32, and the backsheet 33 is then folded over the topsheet 32. In this manner, an edge 34 of the backsheet 33 is defined along the inside of the absorbent article 1, i.e. facing the user of the article.

The embodiment shown in FIG. 1b is configured so that the elastic waist component 23 is fully enclosed by means of the topsheet 32 and the folded backsheet 33. However, according to other embodiments (as will be described below with reference to FIG. 4e), the backsheet 33 and the elastic waist component 23 may be dimensioned and configured so that the backsheet 33 is folded in a manner so as to enclose only a part of the elastic waist component 23.

A similar folding process is carried out also as regards the front portion 3, so that the backsheet 33 forms a fold defining an edge 35 (see FIG. 1a) along the inside of the absorbent article 1. Furthermore, a similar folding process is carried out also as regards the crotch portion 5, so that a fold is formed with a first edge 36 and a second edge 37 (see FIG. 1a) along the absorbent body 17 in the crotch portion 5. Also, a similar folding process is carried out also so as to enclose the elastic leg component 24 along the leg edges 9, 10.

The purpose of the folding procedure as described above is to allow the elastic elements, i.e. the elastic waist component 23, the elastic leg component 24 and the elastic absorbent body components 25, 26, to be positioned very close to the corresponding edge of the absorbent article 1. This means that the absorbent article 1 can be manufactured in a manner with so that it resembles an ordinary undergarment which has an optimized waist elastic function and which is convenient to wear. By positioning the elastic elements very close to each edge of the article, the amount of unelasticized web material which otherwise may occur along the edges can be avoided. In summary, the absorbent article 1 will be more similar in look and feel to regular underwear, while still offering sufficient protection against urine leakage. Furthermore, in an array of gender-specific absorbent articles, an elastic waist component, an elastic leg component and an elastic absorbent body component can be adapted in a suitable manner in article intended to be worn by a male and female user, respectively.

Consequently, the backsheet 33 or the topsheet 32 is folded along the waist edges 7, 8, leg edges 9, 10 and crotch edges 28, 29 so as to enclose each corresponding elastic element 23, 24, 25, 26. Certain alternative embodiments will be further described below.

Also, as mentioned initially, there is a requirement for producing absorbent articles which are similar to conventional underwear, i.e. having a look and feel corresponding to normal male and female underwear and which are adapted to male and female users. Consequently, there are requirements to provide an array, or a set, of gender-specific absorbent articles which are customized for male and female users, respectively, while still allowing an efficient manufacturing process, substantially without any time-consuming and costly modifications of the manufacturing process, for example during a change from production of a male article to a female article.

Figure 3:
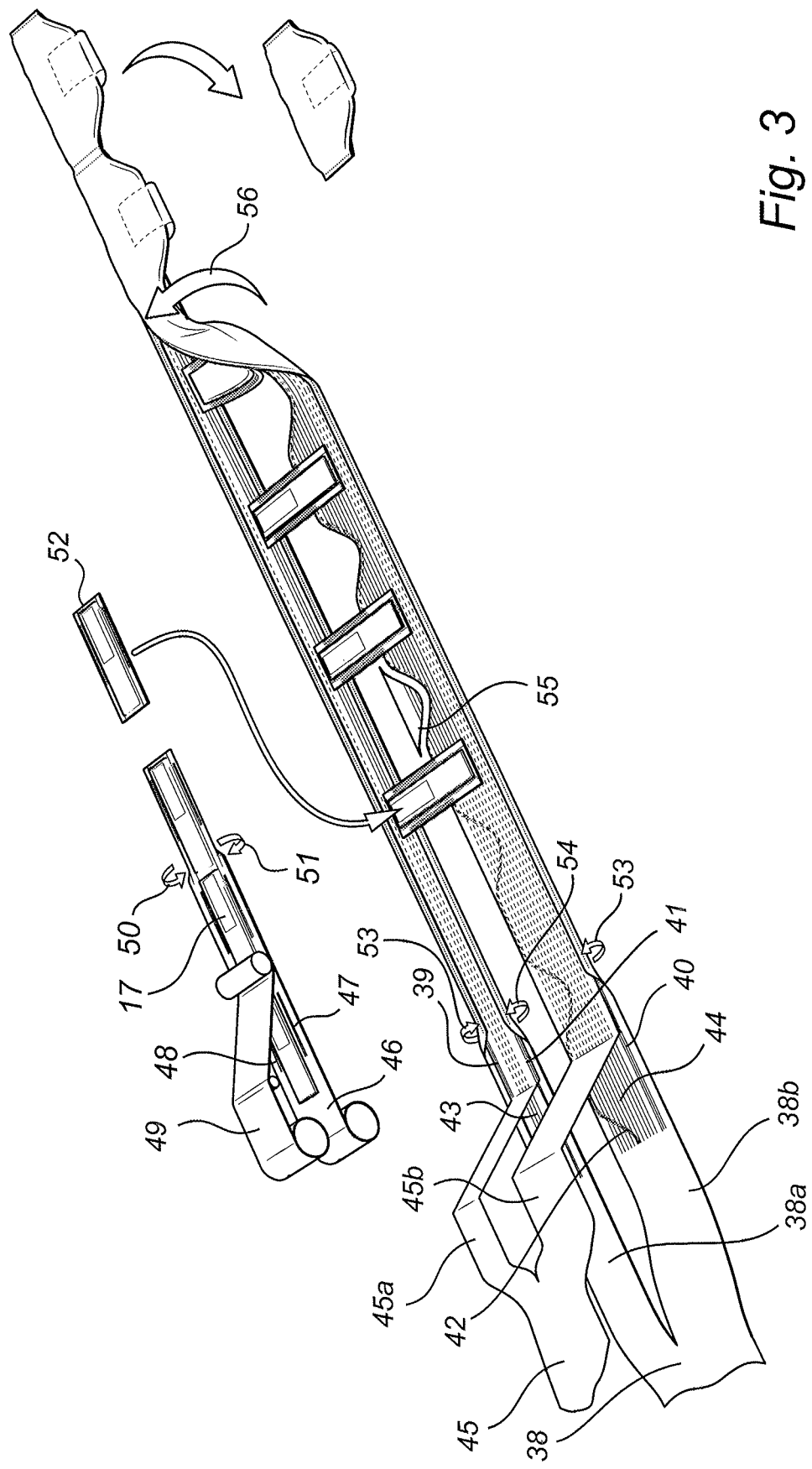
FIG. 3 shows a schematic illustration of a manufacturing process for an absorbent article according to the disclosure.

As mentioned, the positions and the elastic properties of at least the elastic threads forming the front elastic component 30 and the back elastic component 31 can be varied in order to provide articles which are adapted to the male and female anatomy and to other requirements regarding male and female absorbent products. An example embodiment of a manufacturing line for a pant-type absorbent article 1 is schematically illustrated in FIG. 3. A first continuous sheet 38 of web material is supplied and is also divided, in a lengthwise manner, so as to form a first web section 38a and a second web section 38b. The first web section 38a forms the basis of a backsheet for the front portion 3 (see FIGS. 1a and 2) of the absorbent article 1, whereas the second web section 38b forms the basis of a backsheet for the back portion 4.

A plurality of strips of elastic material are attached to the first and second web sections 38a, 38b in a tensioned state. More precisely, a first strip 39 and a second strip 40 of elastic material form the basis of the elastic waist component 23, and a third strip 41 and a fourth strip 42 of elastic material form the basis of the elastic leg component 24. Also, a fifth strip 43 and a sixth strip 44 of elastic material form the basis of the front elastic component 30 and the back elastic component 31, respectively.

The strips 39, 40, 41, 42, 43, 44 of elastic material may be glued or otherwise fastened to the continuous sheets 38a, 38b of web material, and said strips are intended to form an elastic web feature of the absorbent article 1 as described above with reference to FIGS. 1a, 1b and 2.

Next, a further continuous sheet 45 of web material is provided and is split longitudinally in order to form a third web section 45a and a fourth web section 45b. The third web sections 45a forms the basis of a topsheet for the front portion 3 whereas the fourth web section 45b forms the basis of a topsheet for the back section 4.

The third web section 45a and the fourth web section 45b are joined to the first web section 38a and the second web section 38b, respectively, in order to form a laminated product having the strips 39, 40, 41, 42, 43, 44 of elastic material sandwiched between the first web section 38a and the third web section 45a, and also between the second web section 38b and the fourth web section 45b. The second sheets may be attached to each other by ultrasonic bonding, welding, adhesive, embossing, mechanical fastening, or the like. The attachment of the above-mentioned web sections and elastic strips is here described as being performed in consecutive steps but these steps are typically performed in a single step.

In order to form the crotch portion 5 (see FIG. 1a) with its absorbent core 17, a third continuous sheet 46 of web material is provided and forms the basis of a backsheet for the crotch portion 5. The absorbent core 17 is then laid out on the third continuous sheet 46. Also, a seventh strip 47 and an eighth strip 48 of elastic material are also laid out on the third sheet 46 of web material. The seventh strip 47 of elastic material forms the basis of the first absorbent body elastic 25 (see FIGS. 1a and 2), whereas the eighth strip 48 of elastic material forms the basis of the second absorbent body elastic 26.

Next, a fourth continuous sheet 49 of web material is provided and is joined to the third continuous sheet 46, suitably in a manner which is similar to that described above with reference to the first web section 38a, the second web section 38b, the third web section 45a and the fourth web section 45b. During this process, the seventh strip 47 and eighth strip 48 of elastic material, as well as the absorbent core 17, are sandwiched between said third continuous sheet 46 of web material and said fourth continuous sheet 49 of web material.

In order to adapt the manufacturing process to a male-type article and a female-type article, respectively, the process can be modified by choosing suitable elastic material (i.e. for the strips 39, 40, 41, 42, 43, 44 of elastic material) to be included in the articles. Such selections of elastic material according to dimensions, brand, elastic properties and other parameters must be implemented in the manufacturing process in an efficient manner generally without any interruptions or time-consuming modifications.

A folding procedure is next carried out so as to fold the edges of the crotch portion 5 and form the edges 36, 37 on the crotch portion 5. This folding operation is indicated in a simplified manner with the arrows 50 and 51 in FIG. 3. Similarly, folding of the front portion 3 and the back portion 4 is indicated in FIG. 3 with arrows 53, 54 in a simplified manner. This folding operation corresponds to that which is shown in FIG. 1b.

In a further manufacturing step, the web formed by means of the third sheet 46 of web material, the fourth sheet 49 of web material 49 and the absorbent core 17, is cut into individual pieces 52, each of which forms the above-mentioned crotch portion 5 which is subsequently attached to the web formed by the first and second web sections 38a, 38b and the third and fourth web sections 45a, 45b. In this regard, the crotch portions 5 are laid out at a predetermined distance so as to bridge the front portion 3 and the back portion 4 and to form the basis of the finished absorbent article. As shown in FIG. 3, a piece 52 which forms a crotch portion 5 is laid out in a transversal direction in relation to the webs forming the front portion and the back portion.

The crotch portion 5 may be attached to the chassis using any known fastening technology, such as ultrasonic bonding, welding, adhesive, embossing, mechanical fastening, or the like. In this manner, a complete chassis is formed for the article 1 in question.

In a subsequent manufacturing step, leg openings 55 are cut out of the laminated web material forming the chassis of finished absorbent articles. The cutting may be performed by any type of suitable cutting equipment (not shown in FIG. 3), such as rolling cutting using two opposite rollers.

Next, the first and fourth web sections 38b, 45b are folded to form the final product, such that the first web section 38b becomes a backsheet of the chassis and the fourth web section 45b becomes the topsheet of the chassis. This folding is shown with an arrow 56 in FIG. 3. After for example welding of side seams, the continuous assembly of products is cut into individual absorbent articles by means of cutting equipment (not shown in FIG. 3).

FIGS. 4a-f show cross-sectional views of alternative embodiments of the structure forming the back portion 4. FIG. 4a shows an embodiment in which the elastic element 23 is sandwiched between an inner side of the backsheet 33 and an inner side of the topsheet 32. The above-mentioned back elastic component 31 is also shown in FIG. 4a. Also, the backsheet 33 is folded over an outer side of said topsheet 32 so as to enclose the elastic element 23 and so as to define the edge 34. This procedure corresponds to the embodiment shown in FIG. 1b and FIG. 3.

Furthermore, FIG. 4b shows an alternative embodiment in which the elastic element 23 is enclosed and covered within a fold which is defined by the backsheet 33. Subsequently, the topsheet 32 is attached to said backsheet 33, suitably by gluing.

FIG. 4c shows a further alternative embodiment in which the elastic element 23 is sandwiched between an inner side of the backsheet 33 and an inner side of the topsheet 32, and wherein the topsheet 32 is then folded over an outer side of said backsheet 33 so as to enclose the elastic element 23.

FIG. 4d shows a further alternative embodiment which generally corresponds to the embodiment shown in FIG. 4a, but having a back elastic component 31a which is in the form of a relatively thin strip manufactured from an elastically stretchable film. As an example, a suitable thermoplastic elastomer can be used for such a stretchable film.

Furthermore, FIG. 4e shows a further alternative embodiment which generally corresponds to the embodiment shown in FIG. 4a but which shows a configuration in which the backsheet 33 is folded in a manner so that it partly encloses the elastic element 23. Consequently, this embodiment is arranged with a backsheet 33 and an elastic element 23 having other dimensions and configurations than the embodiment shown in FIG. 4a, so that the edge 34 is closer to the waist edge 8 (see also FIG. 1b) as compared with the embodiment in FIG. 4a. Even though the elastic element 23 is only enclosed partly by the folded portion of the backsheet 33, the article can be designed in a manner which is similar to regular underwear while still providing relevant protection against incontinence and also sufficient comfort and fit.

Variations of the embodiments shown in FIGS. 4d and 4e but where the topsheet and backsheet are folded as in FIG. 4b and FIG. 4c, respectively, are also possible within the scope of the invention.

FIG. 4f shows an embodiment in which the elastic element 23 is positioned at a certain distance d from the inside of the fold 33a which is defined by the backsheet 33. According to embodiments, the distanced from the inside of the fold 33a is less than 10 mm in an embodiment, preferably less than 5 mm in another embodiment, and most preferably less than 3 mm in yet another embodiment, in order to provide an absorbent article 1 which is similar to regular underwear while still offering sufficient protection against urine leakage.

Furthermore, FIG. 5 shows a cross-sectional view of an embodiment involving the crotch section 5 and in particular showing the second absorbent body elastic 26 (see also FIG. 1a and FIG. 2). According to this embodiment, the crotch portion comprising a further web material 58 which is folded over the laminate which is defined by the topsheet 32 and the backsheet 33. In this manner, the second absorbent body elastic 26 is enclosed. According to a further embodiment, the crotch portion 5 can be equipped with so-called standing gathers comprising elastic elements 57 which are enclosed by a section of the further web material 58 which is attached to the topsheet 32 by means of adhesive 59 or another suitable fastening means. A similar arrangement can be made as regards the first absorbent body elastic 25 (see FIG. 1a and FIG. 2).

Figure 6A:
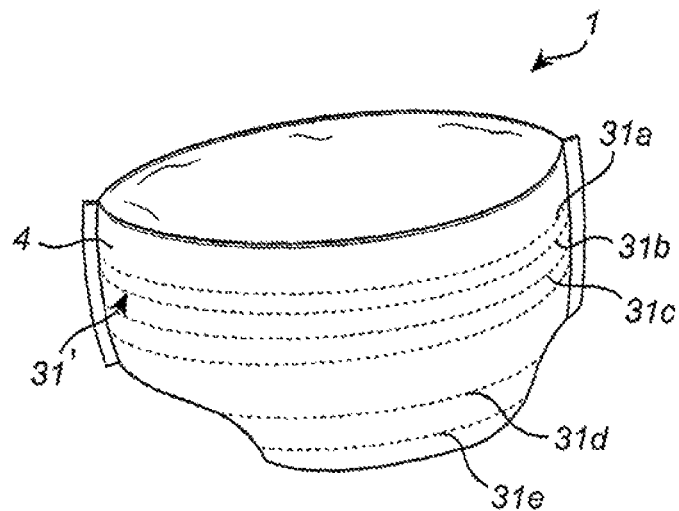
FIG. 6a is a perspective view of the absorbent article as seen from the rear, showing a first configuration which is adapted for the male anatomy.
Figure 6B:
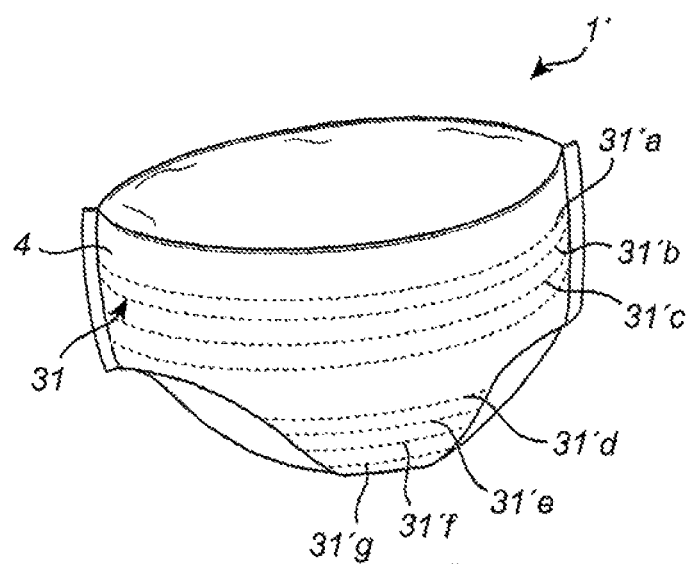
FIG. 6b is a perspective view of the absorbent article as seen from the rear, showing a second configuration which is adapted for the female anatomy.

FIG. 6a and FIG. 6b are perspective views, as regarded from the rear of an absorbent article 1, 1', wherein FIG. 6a shows a first configuration of an embodiment of the absorbent article 1 according to the invention and FIG. 6b shows a second configuration of an embodiment of the absorbent article 1'. The first configuration describes a male type of absorbent article 1, whereas the second configuration describes a female type of absorbent article 1'.

As indicated in FIG. 6a, the article 1 is provided with a back elastic component 31 which according to an embodiment comprises an upper section with a plurality of elastic threads 31a, 31b, 31c etc., which are mounted along the article 1 at a predetermined distance from each other, and also a lower section with a further plurality of elastic threads 31d, 31e, which are also mounted at a predetermined distance from each other. The elastic threads are mounted during the manufacturing process, as described above with reference to FIG. 4, in a generally parallel manner in the back portion 4, i.e. around the region of the article 1 which corresponds at least to the backside of the user. The distance between the elastic threads 31a-e and the extension of said threads 31a-e are chosen so as to suit a male user, i.e. adapted for the male anatomy and requirements regarding style, cut, comfort and fit for a male user. Also, the elastic properties of the elastic threads 31a-e, in particular as regards the dimensions, elastic force and choice of material, are selected in a corresponding manner to suit a male user of the article 1.

Referring now to FIG. 6b, which is an article 1' suitable for a female user, it can be seen that this article 1' has a design which is similar to the article 1 shown in FIG. 6a, i.e. including a back elastic component 31' comprising an upper section with a plurality of elastic threads 31'a, 31'b, 31'c etc. which are positioned in the same manner as the upper section shown in FIG. 6a. However, the back elastic component 31' comprises a lower section which is different from the lower section shown in FIG. 6a. More precisely, the lower section of the back elastic component 31' in FIG. 6b has a higher number of elastic threads 31'd, 31'e, 31'f, 31'g than the lower section shown in FIG. 6a. Also, the threads 31'd, 31'e, 31'f, 31'g in FIG. 6b may be of different type than the threads shown in FIG. 6a in order to adapt the article 1' according to FIG. 6b for the female anatomy and also requirements regarding style, cut, comfort and fit suitable for a female user.

Also, although not visible in FIG. 6b, the elastic threads 31'd, 31'e, 31'f, 31'g of the lower section in FIG. 6b may also have elastic properties—i.e. as regards the dimensions, elastic force and choice of material—which are suitable for a female user and which properties consequently are different than those of the corresponding elastic threads 31d, 31e shown in FIG. 6a.

Consequently, an array of gender-specific absorbent articles is provided by means of the above-mentioned articles 1, 1' shown in FIGS. 6a and 6b. In particular, the lower section in FIG. 6b is pulled tighter together by means of the elastic threads 31'd, 31'e, 31'f, 31'g, as compared with the corresponding lower section in FIG. 6a, so as to form the article 1' in FIG. 6b more suitable for a female user.

The male and female absorbent articles 1, 1' may differ as regards various features, for example:
  the number of elastic threads used in the back elastic components 31, 31';
  the elastic properties of the elastic threads 31, 31';
  the positioning of the threads and the distance between adjacent threads.

For example, the absorbent article 1 in FIG. 6a may have a lower section with two elastic threads, whereas the corresponding lower section in the absorbent article 1' shown in FIG. 6b may have four elastic threads.

Combinations of different features can be made in order to meet the requirements for male and female absorbent products.

Furthermore, according to an embodiment, a male article 1 (see FIG. 6a) may comprise a number of elastic threads of approximately 540 dtex, whereas a female article 1' (see FIG. 6b) may comprises a number of elastic threads of approximately 800 dtex, where dtex represents a unit of the linear density of a continuous filament or yarn of the corresponding elastic thread. This means that the lower section of the female article 1' is configured so as to provide a higher elastic force—as indicated by means of arrows in FIG. 6*b*—to pull the lower section of the article 1' together to fit a female wearer.

Furthermore, although not shown in FIGS. 6*a* and 6*b*, it should be noted that the upper sections of the male and female articles 1, 1' also may have different elastic properties, i.e. in a similar manner as the lower sections.

FIG. 6*a* and FIG. 6*b* indicate that the articles 1, 1' for male and female users, respectively, are slightly different in cut and design. It should be noted that the above-mentioned adaptations for male and female users, respectively, are made without departing from the goal of an efficient manufacturing process as discussed above.

According to an embodiment, a manufacturing process in which a change between production of a male and a female product must be carried out can be made by simply switching the elastic threads adapted for a male article for other elastic threads (having other dimensions or elastic properties) adapted for a female article. Alternatively, the distance between the threads can be changed during such an operation. This also means that the leg opening of the articles can be cut in a similar manner, and with the same equipment, for both male and female articles.

The invention is not limited to the embodiment but can be varied within the scope of the appended claims. For example, the principles of the present invention are equally applicable to any type of hygienic absorbent article. Such articles include various types of incontinence liners and pads, and also sanitary napkins, menstrual pads, panty liners or similar products which are worn inside a supporting panty or which a holder. Such articles also include baby diapers with tape fasteners, pant diapers, training pants, belted diapers or similar disposable absorbent garments.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

The invention claimed is:

1. An array of gender-specific pant type disposable absorbent articles, said array comprising:
   a first disposable absorbent article adapted to be worn by males, the first article having, in its longitudinal direction, a front portion, a back portion and a crotch portion between the front portion and the back portion, and a first elastic component configured for providing fit and comfort of the article to a male user; and
   a second disposable absorbent article adapted to be worn by females, the article having, in its longitudinal direction, a front portion, a back portion and a crotch portion between the front portion and the back portion, and a second elastic component configured for providing fit and comfort of the article to a female user;
   said first elastic component comprising a first plurality of elastic elements extending at least partly along the first article and said second elastic component comprising a second plurality of elastic elements extending at least partly along the second article;
   said first elastic component forming part of at least the back portion of the first absorbent article and said second elastic component forming part of at least the back portion of the second absorbent article;
   wherein the first elastic component is divided into an upper section of elastic elements and a lower section of elastic elements, and the second elastic component is divided into an upper section of elastic elements and a lower section of elastic elements; and the lower section of the first elastic component and the lower section of the second elastic component differ from each other by at least one of the following: i) a positioning of said lower section of elastic elements; and ii) an elastic strength of said lower section of elastic elements,
   wherein said first plurality of elastic elements in the lower section of elastic elements extends in a generally parallel manner along said first article and said second plurality of elastic elements in the lower section of elastic elements extends in a generally parallel manner along said second article.

2. The array according to claim 1, wherein each of said first disposable absorbent article and said second disposable absorbent article comprises a fluid permeable topsheet, a fluid impermeable backsheet, and an absorbent core enclosed between the topsheet and the backsheet.

3. The array according to claim 2, wherein, for each of said first absorbent article and said second absorbent article, the front portion and back portion define a waist edge and a leg edge, and the crotch portion defines two crotch edges, and wherein a waist elastic component extends along the waist edge, a leg elastic component extends along the leg edge and a first absorbent body elastic component and a second absorbent body elastic component extend along each one of the crotch edges, and said backsheet or said topsheet is folded along said waist edge, leg edge and crotch edges so as to enclose at least a part of each corresponding elastic component.

4. The array according to claim 1, wherein the first plurality of elastic elements in the lower section comprises adjacent elastic threads located a first distance from each other and the second plurality of elastic elements in the lower section comprises adjacent elastic threads located a second distance from each other, and the first distance is different from the second distance.

5. The array according to claim 1, wherein said first elastic component and said second elastic component comprise different dimensions, or different materials, or different elastic forces, thereby providing said different elastic strength of the first and second lower sections of elastic elements.

6. The array according to claim 1, wherein said first and second absorbent articles comprise incontinence articles.

7. The array according to claim 1, wherein the first disposable absorbent article comprises first leg elastics, which are distinct from the first elastic component, and wherein the second disposable absorbent article comprises second leg elastics, which are distinct from the second elastic component.

8. The array according to claim 1, wherein the lower section of the first elastic component and the lower section of the second elastic component differ from each other by the positioning of said lower section of elastic elements.

9. The array according to claim 1, wherein the lower section of the first elastic component and the lower section of the second elastic component differ from each other by the elastic strength of said lower section of elastic elements.

10. A method for manufacturing an array of gender-specific pant type disposable absorbent articles, said method for manufacturing the array of gender-specific pant type disposable absorbent articles comprising:
producing a first disposable absorbent article adapted to be worn by males, the first article having, in its longitudinal direction, a front portion, a back portion and a crotch portion between the front portion and the back portion, and a first elastic component configured for providing fit and comfort of the first article to a male user;
producing a second disposable absorbent article adapted to be worn by females, the second article having, in its longitudinal direction, a front portion, a back portion and a crotch portion between the front portion and the back portion, and a second elastic component configured for providing fit and comfort of the second article to a female user;
wherein producing the first disposable absorbent article comprises providing a first plurality of elastic elements forming part of said first elastic component and extending at least partly along said first article, and attaching said first elastic component to part of at least the back portion of the first absorbent article; and
wherein producing the second disposable absorbent article comprises providing a second plurality of elastic elements forming part of said second elastic component and extending at least partly along said second article, and attaching said second elastic component to part of at least the back portion of the second absorbent article;
wherein the first elastic component is divided into an upper section of elastic elements and a lower section of elastic elements, and the second elastic component is divided into an upper section of elastic components and a lower section of elastic components; and the lower section of the first elastic component and the lower section of the second elastic component are different from each other in at least a positioning of the lower section of elastic elements or in an elastic strength of said lower section of elastic elements,
wherein said first plurality of elastic elements in the lower section of elastic elements extends in a generally parallel manner along said first article and said second plurality of elastic elements in the lower section of elastic elements extends in a generally parallel manner along said second article.

11. The method according to claim 7, wherein the first plurality of elastic elements in the lower section comprises adjacent elastic threads located a first distance from each other and the second plurality of elastic elements in the lower section comprises adjacent elastic threads located a second distance from each other, and the first distance is different from the second distance.

12. The method according to claim 10, wherein the lower section of the first elastic component and the lower section of the second elastic component are different from each other in the positioning of the lower section of elastic elements.

13. The method according to claim 10, wherein the lower section of the first elastic component and the lower section of the second elastic component are different from each other in the elastic strength of said lower section of elastic elements.

14. A method for manufacturing an array of gender-specific pant type disposable absorbent articles, said method for manufacturing the array of gender-specific pant type disposable absorbent articles comprising:
producing a first disposable absorbent article adapted to be worn by males, the first article having, in its longitudinal direction, a front portion, a back portion and a crotch portion between the front portion and the back portion, and a first elastic component configured for providing fit and comfort of the first article to a male user;
changing to producing a second disposable absorbent article adapted to be worn by females, the second article having, in its longitudinal direction, a front portion, a back portion and a crotch portion between the front portion and the back portion, and a second elastic component configured for providing fit and comfort of the second article to a female user;
wherein producing the first disposable absorbent article comprises providing a first plurality of elastic elements forming part of said first elastic component and extending at least partly along said first article, and attaching said first elastic component to part of at least the back portion of the first absorbent article; and
wherein producing the second disposable absorbent article comprises providing a second plurality of elastic elements forming part of said second elastic component and extending at least partly along said second article, and attaching said second elastic component to part of at least the back portion of the second absorbent article;
wherein the first elastic component is divided into an upper section of elastic elements and a lower section of elastic elements, and the second elastic component is divided into an upper section of elastic components and a lower section of elastic components; and the lower section of the first elastic component and the lower section of the second elastic component are different from each other in at least a positioning of the lower section of elastic elements or in an elastic strength of said lower section of elastic elements,
wherein the first disposable absorbent article comprises first leg elastics, which are distinct from the first elastic component, and wherein the second disposable absorbent article comprises second leg elastics, which are distinct from the second elastic component, and
wherein changing between producing the first disposable absorbent article and the second disposable absorbent article comprises a step of changing at least the positioning of the respective lower sections of elastic elements or changing the elastic strength of the respective lower sections of elastic elements.

15. The method according to claim 14, wherein changing between producing the first disposable absorbent article and the second disposable absorbent article comprises a step of changing the positioning of the respective lower sections of elastic elements.

16. The method according to claim 14, wherein changing between producing the first disposable absorbent article and the second disposable absorbent article comprises a step of changing the elastic strength of the respective lower sections of elastic elements.

* * * * *